United States Patent [19]

Noonan et al.

[11] Patent Number: 6,129,896
[45] Date of Patent: Oct. 10, 2000

[54] BIOSENSOR CHIP AND MANUFACTURING METHOD

[75] Inventors: Timothy Noonan, Worcester; James Noonan, Spencer, both of Mass.

[73] Assignee: Drawn Optical Components, Inc., Worcester, Mass.

[21] Appl. No.: 09/213,587

[22] Filed: Dec. 17, 1998

[51] Int. Cl.[7] .................................................. G01N 33/53
[52] U.S. Cl. ......................... 422/82.05; 436/86; 436/94; 436/164
[58] Field of Search ........................... 422/82.05; 436/86, 436/87, 88, 89, 90, 94, 164; 427/165, 169

[56] References Cited

U.S. PATENT DOCUMENTS

| | | | |
|---|---|---|---|
| 4,103,064 | 7/1978 | McAlear et al. | 428/333 |
| 4,302,530 | 11/1981 | Zemel | 430/311 |
| 4,562,157 | 12/1985 | Lowe et al. | 435/291 |
| 4,908,112 | 3/1990 | Pace | 204/299 |
| 5,200,051 | 4/1993 | Cozzette et al. | 204/403 |
| 5,320,814 | 6/1994 | Walt et al. | 422/82.07 |
| 5,545,531 | 8/1996 | Rava et al. | 435/6 |
| 5,585,069 | 12/1996 | Zanzucchi et al. | 422/100 |
| 5,661,028 | 8/1997 | Foote | 435/287 |
| 5,690,894 | 11/1997 | Pinkel et al. | 422/68.1 |
| 5,736,257 | 4/1998 | Conrad et al. | 428/474.4 |
| 5,760,130 | 6/1998 | Johnston et al. | 525/54.2 |
| 5,837,196 | 11/1998 | Pinkel et al. | 422/55 |
| 5,874,219 | 2/1999 | Rava et al. | 435/6 |

FOREIGN PATENT DOCUMENTS 9955460  11/1999  WIPO .

OTHER PUBLICATIONS

Nicholas Wade, "Where Computers and Biology Meet: Making a DNA Chip", Apr. 8, 1997, New York Times.
Stanford University Medical Center Office of Communications, "Silicon Chip Scans Thousands of Genes at Once, Speeding Genetic Studies", Dec. 9, 1996.
Correspondent Dick Wilson, "Scientists Developing a Lab-On-A-Chip", Feb. 11, 1997, Oak Ridge, Tennessee (CNN).
"Scientists Say Tiny Sensor Has Giant Potential", Nov. 20, 1996, Atlanta, Georgia (CNN).
Tech Resources, "To Know Ourselves: Tools of the Trade".
Carolyn Krause, "ORNL's Law on a Chip Analyzes DNA in a Droplet", Mar. 26, 1996, Oak Ridge, Tennessee.
Sally Pobojewski, "U-M Researchers Try to Create DNA-Analyzing Microchip", Jun. 11, 1996, The University Record, University of Michigan.
Doctor's Guide to Medical and Other News, "DNA Biochip Provides Blood Test Answers in Minutes", Dec. 11, 1997, Oak Ridge, Tennessee.
D&MD Reports, International Business Communications, Inc., "Biochip Technologies and Their Commercial Applications—Capitalize on Revolutionary New Tools for Drug Discovery and Diagnostic Testing", Oct., 1997.
PBS Online Innovation, Technology Update, "DNA Chip Breakthrough".

*Primary Examiner*—Jeffrey Snay
*Attorney, Agent, or Firm*—Bourque & Associates, P.A.

[57] ABSTRACT

A new biosensor device and biosensor device manufacturing method improves upon the prior art by providing high reliability devices that can be manufactured on an extremely low cost basis and which are amenable to quality control procedures, which can be performed on individual fibers as well as the devices themselves. The improved biosensor devices are manufactured by first synthesizing a plurality of functional moieties onto a plurality of fibers, which may be solid and/or hollow, wherein at least one fiber receives one moiety. Once the functional moieties are synthesized onto the fibers, the fibers are bundled in a predetermined arrangement. The bundled fibers are then bonded or fused together to fix their predetermined arrangement. Finally, the bonded fiber bundle is sliced into a plurality of individual devices or chips.

21 Claims, 3 Drawing Sheets

BIOSENSOR CHIP AND MANUFACTURING METHOD

FIELD OF THE INVENTION

This invention relates to a device which can serve as a biosensor device and which is useful for separation and detection of micro quantities of proteins and similar types of genetic materials and organic molecules and to a method of manufacturing such a device, which can be implemented as microarrays which may be used for high throughput screening applications, bioremediation and detection and quantification.

BACKGROUND OF THE INVENTION

There exists a need for reliable, low cost analytical devices that allow for the rapid separation and detection of micro quantities of cellular tissue, genetic material, organic molecules, sequencing, etc. for use in research as well as in the diagnosis of disease(s) or the existence of certain predetermined conditions. DNA analysis is an effective approach for the detection and identification of viruses, bacteria, and other microbes and is essential to the identification of genetic disorders. The ability to detect DNA with a high level of specificity entails high resolution separation of RNA or DNA fragments, appropriate labeling chemistry for such fragments and the adaptation of high sensitivity sensors that are specific for the labeling chemistry employed. DNA probe technology is now an established tool of the molecular biologist for revealing the presence of diagnostically significant cells, whether they be diseased cells from the subject or infectious micro organisms.

Recently, DNA analysis devices have experienced a miniaturization trend similar to that experienced in the electronics industry with the advent of integrated circuits. Many of the same principles that have led to smaller and smaller micro processor devices have shrunk the size of a chemistry lab to a device no larger than the size of a dime. The techniques are all aimed at producing a device having different, discreet areas that are sensitive to different genetic sequences. These areas, or probes, are formed using a number of techniques, including photo patterning methods, such as photolithography, which is a direct descendant from techniques used in the manufacture of micro processor chips; micro machining, where tiny channels are machined into a chip to hold various test media; and other methods of precisely depositing test media upon chips in a precisely defined pattern.

While these methods do allow for the manufacture of acceptable biosensor chips, they do have a number of drawbacks. One significant drawback is the sophistication and expense of photo patterning, micro machining and micro-media deposition devices that are capable of producing biosensor chips including hundreds or thousands of individual probes. Additionally, the use of these prior art methods requires extreme precision in the deposition of test materials since their deposition involves microscopic quantities and positions. This also leads to significant quality control issues, since a single biosensor chip can have literally thousands of separate probes, each of which requires testing or verification.

Due to these drawbacks and limitations, biosensor chips are expensive to manufacture and although they provide significant improvements in the state of the art, they have not yet experienced wide scale implementation. In addition, the technology is too expensive for implementation with respect to low cost diagnostic tests.

Accordingly, there is a need for an improved biosensor chip or device and method of manufacturing the same, which can result in inexpensive biosensor devices that can be manufactured using cost effective machinery. Additionally, there is a need for a biosensor device that can be highly reliable due to improved quality assurance procedures performed during the manufacture thereof. Finally, a biosensor device is needed that can utilize the same manufacturing methods for a wide variety of analysis protocols including both sophisticated and simple analytical procedures.

SUMMARY OF THE INVENTION

The disclosed invention provides a new biosensor device which improves upon the prior art by providing high reliability sensors that can be manufactured on an extremely low cost basis. The improved biosensor devices are manufactured by first synthesizing a plurality of functional moieties onto a plurality of fibers, wherein each fiber receives one moiety. Once the functional moieties are synthesized onto the fibers, the fibers are bundled in a predetermined arrangement. The bundled fibers are then bonded together to fix their predetermined arrangement. Finally, the bonded fiber bundle is "sliced" into a plurality of devices (chips). In one preferred embodiment, the fibers comprise glass fibers.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
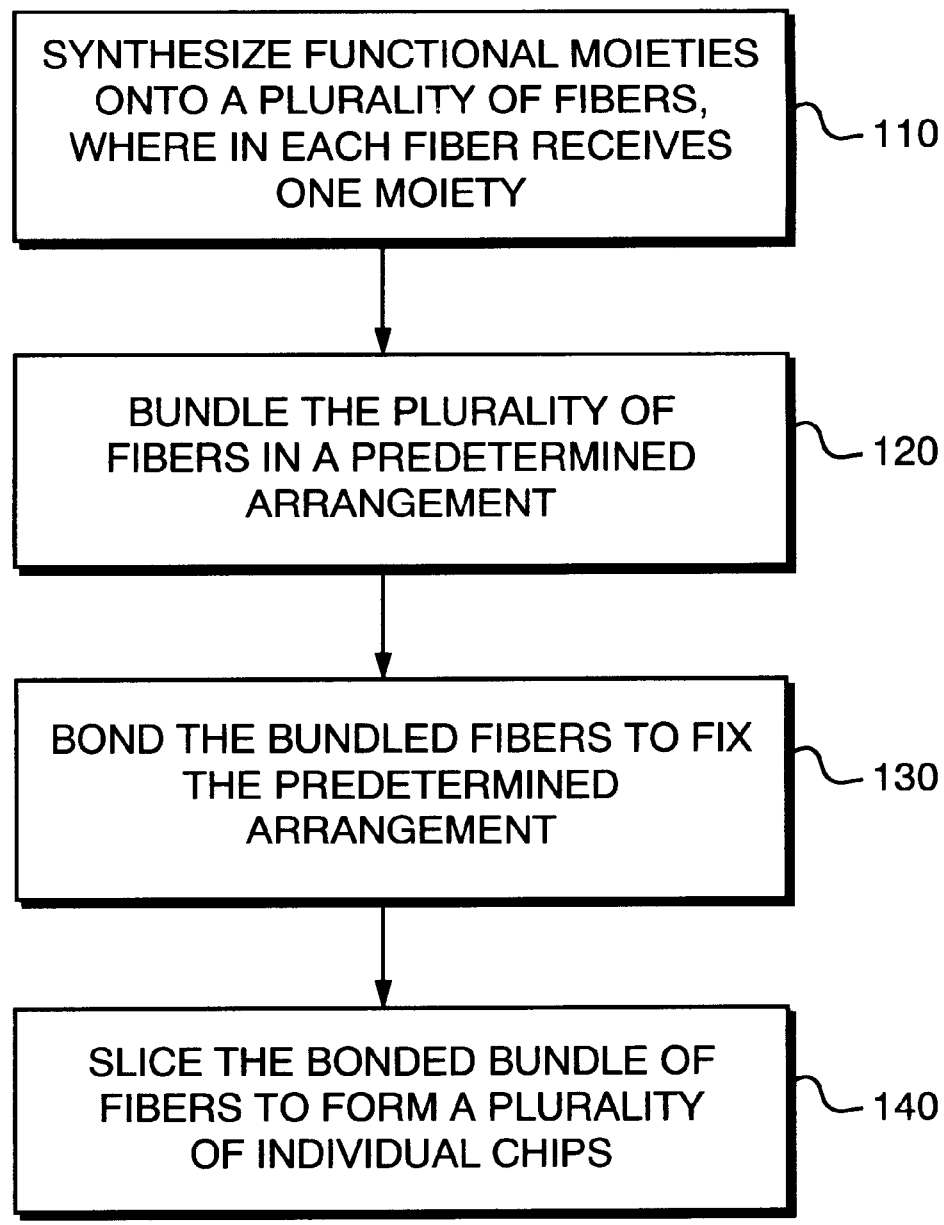
FIG. 1 is a flow diagram showing the steps included in the disclosed method of manufacturing a biosensor device.
Figure 3:
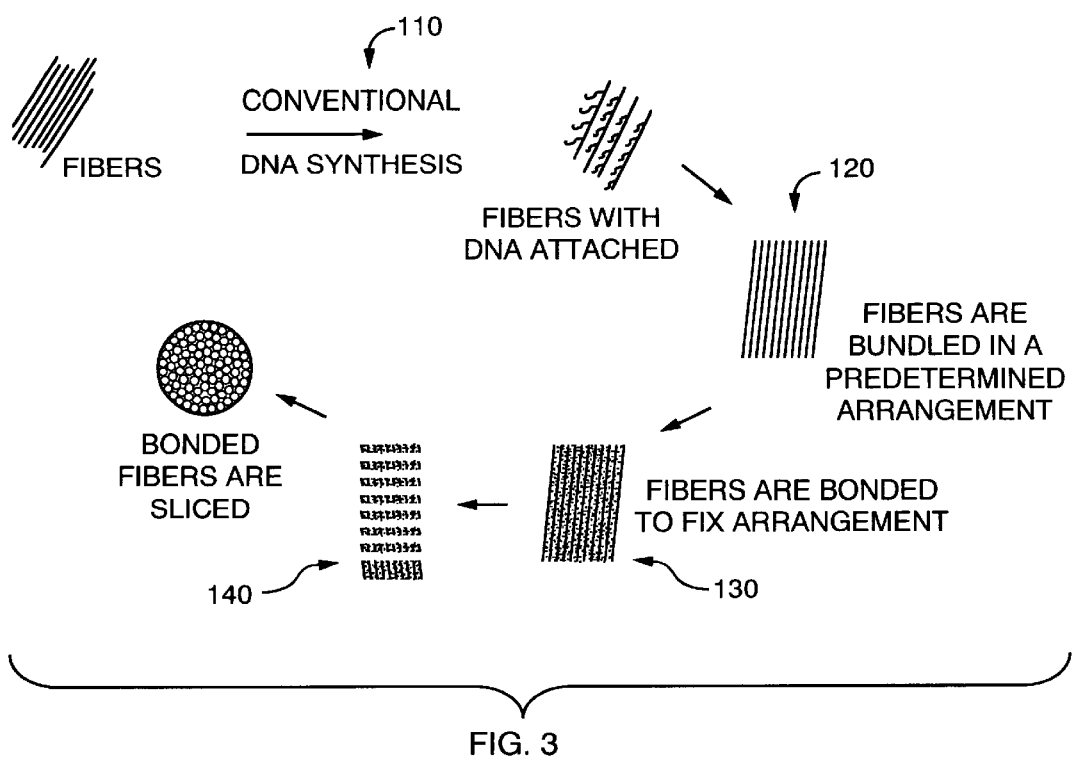
FIG. 3 is a functional block diagram of the disclosed method of manufacturing biosensor devices.

Turning now to the Figures, and in particular FIGS. 1 and 3, an improved method of manufacturing a biosensor device is disclosed. Method 100 begins by synthesizing functional moieties onto a plurality of fibers, step 110. The fibers can be various diameters and may be solid or hollow. At least one fiber receives several moieties of the same species. However, as will become evident below, more than one fiber may receive the same functional moiety. The functional moieties selected will be dependent upon the specific testing protocol or protocols for which the biosensor device is designed.

For example, functional moieties may include DNA oligonucleotides for DNA testing biosensor devices. Alternatively, the functional moieties may include proteins, peptides, antibodies or other chemical functional groups. In the preferred embodiment, the fibers comprise glass fibers. However, the principles of the invention are equally applicable to polymer fibers or other similar elongated fibers.

Once the fibers are synthesized with their respective functional moieties, the fibers are bundled into a predetermined arrangement, step 120, such as a circle, square, etc. The bundled fibers are then bonded to fix the predetermined arrangement, step 130. Bonding may include fiber fusion or any one of a number of well known biologically inert bonding adhesives such as polysulfone adhesive available from Huls of Germany under the brand name glassclad, or other biologically inert adhesive used in the biopharmaceutical industry. The biologically inert bonding medium thus fills the interstices intermediate the plurality of fibers, thereby separating the functional moieties on the plurality of fibers included in the bundle.

Once the bundled fibers are adequately bonded and their predetermined arrangement is fixed, the fiber bundle is sliced, step 140, to form a plurality of individual "chips" or devices. The slices may be along an axis perpendicular to a longitudinal axis of the fibers. Thus, each individual biosensor device may include a portion of each fiber included in the fiber bundle. Of course, different slicing orientations will result in biosensor devices having different configurations. In fact, the invention contemplates linearly aligned fibers, which are bonded in their linear arrangement. The linearly arranged fiber bundle can then be cut to form wafers having linearly orientated fibers upon which the various functional moieties are synthesized.

Since the arrangement of the fibers is determined during the bundling process, a wide variety of devices may be implemented according to the invention. For example, a device may include many fibers that have the same functional moiety synthesized thereupon. These like fibers can be arranged to form a large region responsive to certain chemicals. Thus, larger, macroscopic biosensor devices can be produced.

On the other extreme, the biosensor devices manufactured according to the principles of the present invention could include literally thousands of fibers synthesized with distinct functional moieties. In this case, analysis of such a biosensor device after it is exposed to a sample would require sophisticated readers and processors, such as lasers, micro computers and optical recognition devices.

In the preferred embodiment, the glass fibers used are selected from the group consisting of lead borosilicate, soda-lime, rare earth lead, rear earth crown, flint, short flint, crowned silica, crown silica and borosilicate. However, the invention is not limited to these specific types of glass.

Figure 2:
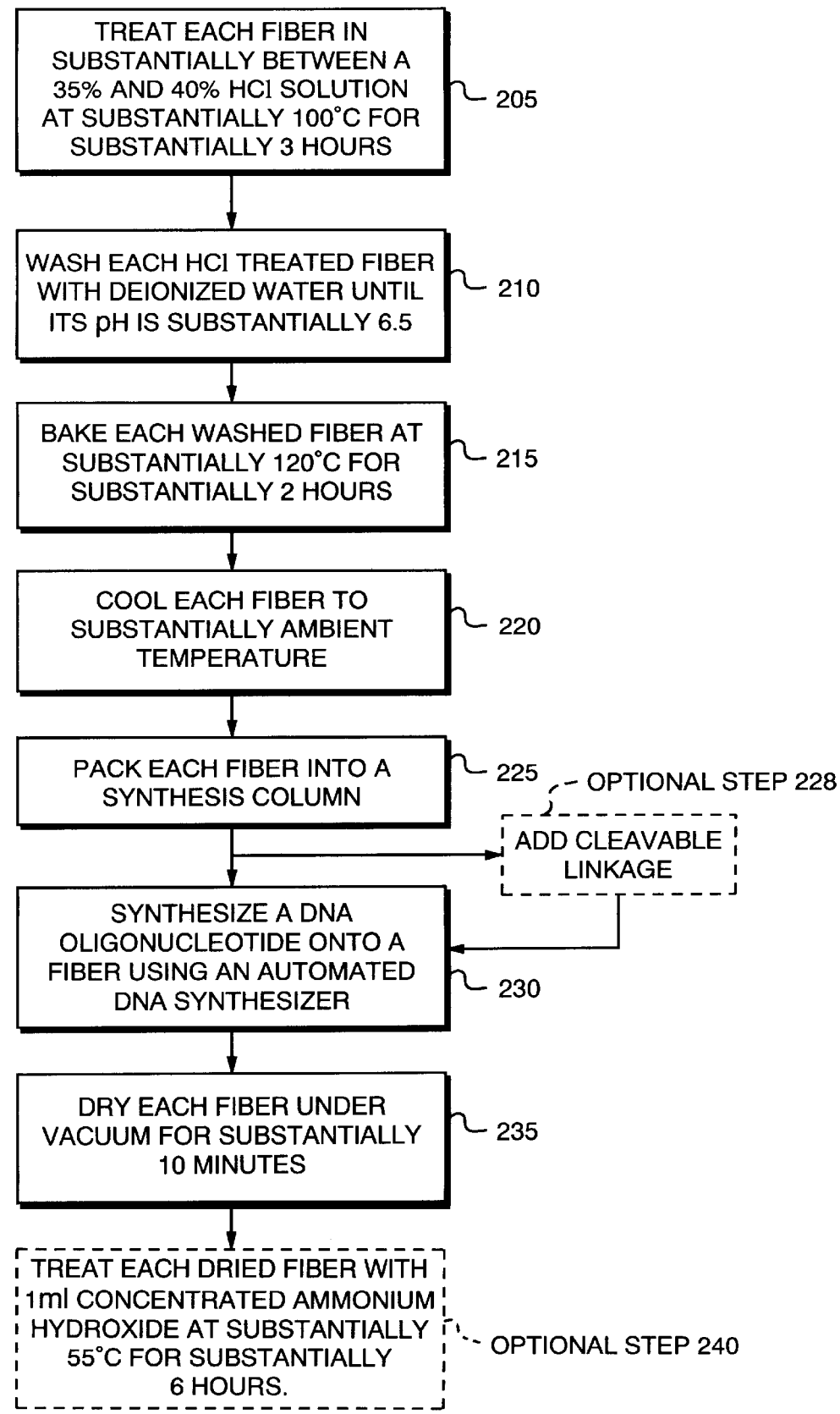
FIG. 2 is a detailed block diagram of a method of synthesizing DNA onto fibers to be included in the biosensor device of the present invention.

FIG. 2 shows, in detail, one embodiment of the step of the invention wherein the functional moieties are synthesized onto the fibers. In the example shown, the fibers include glass fibers and the functional moieties synthesized thereupon comprise DNA oligonucleotides. If the invention is practiced using plastic or polymer fibers, the method 200 would begin with step 225.

In the embodiment of the invention utilizing glass fibers, the method 200 begins by treating each glass fiber in generally a 35 percent and 40 percent HCl solution at substantially 100° C. for substantially three hours, step 205. This step exposes the hydroxy group of the glass fibers. In step 210, each HCl treated glass fiber is washed with deionized water until its pH reaches substantially 6.5. Next, each washed fiber is baked at substantially 120° C. for substantially two hours, step 215.

Thereafter, each fiber is cooled to substantially ambient temperature, step 220. At this point, one can directly go to the synthesis column step 225 or a cleavable linkage may be added to the hydroxyl groups, step 228, which allows for the DNA to be cleaved and analyzed after synthesis, for quality control purposes and the like. Then, in step 225, each glass fiber is packed into a synthesis column, such as a one "µmole" column manufactured by PerSeptive Biosystems.

The fiber is then ready to accept the syntheses of a DNA oligonucleotide.

A DNA oligonucleotide is synthesized onto the fiber, step 230, using an automated DNA synthesizer such as those available from PerSeptive Biosystems or Perkin Elmer. This is accomplished with either the standard protocol or with a minor variation to the manufacture's standard synthesis protocol namely, an increased coupling time. The standard protocol typically has three (3) coupling steps or stages totaling 5 minutes coupling time. The present invention contemplates three (3) coupling stages of 10 minutes, 4 minutes and 1 minute respectively, although this is not a limitation of the present invention. Coupling time is a factor of the fiber type used and whether or not the fibers are hollow or not.

After the DNA synthesis is completed, the column is dried under a vacuum for substantially ten minutes, step 235. As indicated earlier, if quality control measures are to be implemented to the synthesized fibers, then, in optional step 240, the fiber, which now includes a DNA oligonucleotide synthesized thereupon is treated with a one ml concentrated ammonium hydroxide solution at a temperature of substantially 55° C. for a period of substantially six hours. This step will cleave the DNA ologonucleotide (the functional moiety) from the fiber so that it can be analyzed for quality control purposes. Analytical testing, such as absorption measurement of the ammonium hydroxide solution at 260 nm indicates that there is no loss of the DNA oligonucleotide from the glass fiber or if a cleavable linker was added then absorption at 260 nm indicates the presence of DNA.

One of the important improvements over the prior art offered by the disclosed method of making biosensor devices is that they can be manufactured at a low cost, when compared to current manufacturing methods. Another advance, which is again significant is the ability to test the individual fibers before they are formed into a bundle for quality assurance purposes. Testing can be performed by cleaving a functional moiety off of an individual fiber sample and quality control can be performed on the cleaved functional moiety. This is not possible with present biosensor chips, which utilize photolithography or other techniques to bond a plurality of different functional moieties to different locations upon the chip.

Figure 4:
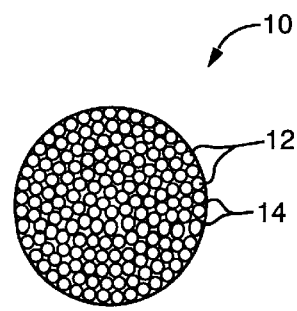
FIG. 4 is a top view of a biosensor device manufactured according to the principles of the present invention.

FIG. 4 shows a biosensor device 10 manufactured according to the principles of the present invention. The biosensor device 10 is comprised of a plurality of individual fibers 12 upon which functional moieties have been synthesized. As explained earlier, the fibers are arranged and bonded in their arrangement using a bonding medium 14, which substantially fills the interstitial spaces intermediate the individual fibers and thereafter allows the fiber bundle to be sliced into individual chips, (step 140, FIG. 3). Step 140 may also be accomplished by glass fusion, as is well know in the art, which serves to "bond" the fibers together.

Thus, the disclosed invention provides a significant improvement over the prior art in providing a cost effective, quality determinative biosensor device and method of their manufacture.

Modifications and substitutions by one of ordinary skill in the art are considered to be within the scope of the present invention which is not to be limited except by the claims which follow.

What is claimed is:

1. A method of manufacturing biosensor device comprising synthesizing one or more functional moiety onto a plurality of fibers, wherein at least one fiber receives one moiety; bundling said plurality of fibers in a predetermined arrangement; bonding or fixing said bundled plurality of fibers to fix the predetermined arrangement; and slicing said bundled fiber bundle into a plurality of biosensor devices.

2. The method of manufacturing biosensor devices of claim 1 wherein the step of slicing said bonded fiber bundle comprises cutting the bundle at an angle such that a portion of each fiber included in the bundle is included in each biosensor device.

3. The method of manufacturing biosensor devices of claim 2 wherein said angle is substantially 90° with respect to a longitudinal axis of the bundled fibers.

4. The method of manufacturing biosensor devices of claim 1, wherein said at least one functional moiety synthesized onto said fibers comprises DNA oligonucleotides.

5. The method of manufacturing biosensor devices of claim 1, wherein said at least one functional moiety comprise proteins.

6. The method of manufacturing biosensor devices of claim 1, wherein said functional moieties comprise peptides.

7. The method of manufacturing biosensor devices of claim 1, wherein said functional moieties comprise antibodies.

8. The method of manufacturing biosensor devices of claim 1, wherein said functional moieties comprise chemical functional groups.

9. The method of manufacturing biosensor devices of claim 4, wherein said step of synthesizing said DNA oligonucleotide onto said fibers comprises:

treating each fiber in substantially between a 35 and 40 percent HCl solution at substantially 100° C. for substantially three hours;

washing each treated fiber with deionized water until the pH of each glass fiber is substantially 6.5;

baking each washed fiber at substantially 120° C. for substantially two hours;

cooling each fiber to substantially ambient temperature; packing each fiber into a 1 $\mu$mole column;

synthesizing a DNA oligonucleotide onto said fiber using an automated DNA synthesizer; and drying said fiber under vacuum for substantially ten minutes.

10. The method of manufacturing biosensor devices of claim 9, further comprising the step of treating said fiber with 1 ml concentrated ammonium hydroxide at substantially 55° C. for substantially six hours.

11. The method of manufacturing biosensor devices of claim 1, wherein said step of bonding said plurality of fibers comprises chemically bonding said fibers using a biologically inert chemical bonding agent, said bonding agent forming biologically inert interstices intermediate the fibers arranging the bundle and thereby separating the functional moieties included on the manufactured biosensor device.

12. The method of manufacturing biosensor devices of claim 1, wherein said fibers are glass fibers, and further wherein said step of bonding said plurality of fibers comprises glass fusing said glass fibers.

13. A method of manufacturing biosensor devices comprising:

applying a plurality of functional moieties onto a plurality of fibers, each of said fibers including a single functional moiety;

arranging said plurality of fibers into a bundle, wherein each said fiber is in a predetermined position;

fixing said fiber arrangement in said bundle using a chemical bonding technique; and slicing said fiber bundle into individual biosensor devices.

14. An improved biosensor device comprising an individual slice of a plurality of individual fibers, each individual fiber having applied thereto a functional moiety, said individual fibers being arranged in a predetermined fashion, and the arrangement fixed by bonding said fibers together.

15. The improved biosensor device of claim 14, wherein said fibers comprise glass fibers.

16. The improved biosensor device of claim 14, wherein said fibers comprise plastic fibers.

17. The improved biosensor device of claim 15, wherein said fibers comprise quartz fibers.

18. The improved biosensor device of claim 14, wherein the glass fibers are selected from the group consisting of lead borosilicate, soda lime, borosilicate, rare earth lead, rear earth crown, flint, shortflint, crown, silica, and fused silica.

19. The improved biosensor device of claim 14 wherein said fibers comprise polymer fibers.

20. The improved biosensor device of claim 14 wherein said fibers comprise hollow fibers.

21. The improved biosensor device of claim 14 wherein said fibers comprise solid fibers.

* * * * *